United States Patent [19]

Lundblad

[11] Patent Number: 4,618,486

[45] Date of Patent: Oct. 21, 1986

[54] MONOCLONAL ANTIBODY FORMULATION FOR DIAGNOSTIC USE

[75] Inventor: Karl A. Lundblad, Upsala, Sweden

[73] Assignee: MonoCarb AB, Lund, Sweden

[21] Appl. No.: 570,264

[22] Filed: Jan. 12, 1984

[30] Foreign Application Priority Data

Jan. 21, 1983 [SE] Sweden ................................ 8300320

[51] Int. Cl.⁴ ................... G01N 33/53; G01N 33/577; G01N 33/555

[52] U.S. Cl. ......................................... 424/11; 435/7; 435/29; 436/513; 436/520; 436/548; 436/808; 436/826

[58] Field of Search ................ 424/11; 435/7, 29, 513, 435/517, 808, 826, 520, 547, 548

[56] References Cited

U.S. PATENT DOCUMENTS 4,164,558  8/1979  non Schulthess et al. ............ 424/11

FOREIGN PATENT DOCUMENTS 8203462  10/1982  PCT Int'l Appl. ................... 424/11

OTHER PUBLICATIONS

Moore, et al. (1976) Transfusion, vol. 16, No. 4 pp. 291–296.
Rock, et al. (1978) Transfusion, vol. 18, No. 2 pp. 228–232.
Jorgensen (1980) Vot Sanguinis, vol. 36, pp. 186–191.
Anstee, D. J.: Characterization of Human Blood Group Alloantigens. Monoclonal Antibodies in Clinical Medicine. (Ed. McMichael, A. J.; Fabre, J. W. Academic Press, London 1982). pp. 237–249.
Voak, D. et al., Monoclonal Anti-A from a Hybrid-Myeloma: Evaluation as a Blood Grouping Reagent. Vox Sang. 39: 134–140 (1980).
Sacks, S. H. et al., Monoclonal Anti-B as a New Blood-Typing Reagent. Vox Sang. 40: 99–104 (1981).
Edelman, L. et al., Thermodynamic and Immunological Properties of a Monoclonal Antibody to Human Blood Group A. Immunology 44: 549–554 (1981).
Bundle, D. R. et al., Hybridomas Specific for Carbohydrates; Synthetic Human Blood Group Antigens for the Production, Selection, and Characterization of Monoclonal Typing Reagents. J. Immunol. 129: 678–682 (1982).
Majdic, O. et al., Hybridomas Secreting Monoclonal Antibodies to Human Group A Erythrocytes. Immunobiology 156: 226–227 (1979).
Voak, D. et al., Monoclonal Anti-A and Anti-B: Development as Cost-Effective Reagents. Med. Lab. Sci. 39: 109–122 (1982).
Stahli, C. et al., High Frequencies of Antigen-Specific Hybridomas; Dependence on Immunization Parameters and Prediction by Spleen Cell Analysis. J. Immunol. Meth. 32; 297–304 (1980).
Dodge, J. T. et al., The Preparation and Chemical Characteristics of Hemoglobin-Free Ghosts of Human Erythrocytes. Arch. Biochem. Biophys. 100: 119–130 (1963).
Nowinski, R. C. et al., The Isolation of Hybrid Cell Lines Producing Monoclonal Antibodies Against the p. 15 (E) Protein of Ecotropic Murine Leukemia. Virology 93: 111–126 (1979).
Kennett, R. H., Monoclonal Antibodies (Ed. Kennett, R. H., McKearn, T. J.; Bechtol, K. B.) Plenum Press, New York 1980, pp. 365–367.
Fazekas de St. Groth, et al., Production of Monoclonal Antibodies: Strategy and Tactics. J. Immunol. Meth. 35: 1–21 (1980).

(List continued on next page.)

Primary Examiner—Esther M. Kepplinger
Assistant Examiner—William J. Herald
Attorney, Agent, or Firm—Burns, Doane, Swecker & Mathis

[57] ABSTRACT

Aqueous formulation containing monoclonal antibodies active against cell-bound antigens, particularly human red cell antigens, the said formulation containing a soluble salt in a concentration of not less than about 200 mmoles/l.

9 Claims, 1 Drawing Figure

OTHER PUBLICATIONS

Engwall, E. et al., Enzyme-Linked Immunosorbent Assay, ELISA. III. Quantitation of Specific Antibodies by Enzymelabeled Anti-Immunoglobulin Antigen-Coated Tubes. J. Immunol. 109: 129–135 (1972).

Ouchterlony, O.: Diffusion-in-Gel Methods for Immunological Analysis I. Progr. Allergy 5: 1–78 (1958).

Messeter, L. et al. Automated Blood Grouping of Patients and Blood Donors Using Groupamatic 360 S and a Separate Minicomputer. Vox Sang. 33: 116–123 (1977).

Race, R. R. et al. Blood Groups in Man. 5th Ed. (Blackwell, Oxford 1968) p. 23.

European Agreement on the Exchanges of Blood-Grouping Reagents. European Treaty Series No. 39 (Council of Europe, Strasbourg, 1962).

Gooi, H. C. et al. Natural Antibodies as Contaminants of Hybridoma Products, Biochem. Biophys. Res. Comm. 106: 539–545 (1982).

Lennox, S.: Personal Communication, Hughes-Jones, N. C. et al. Optimal Conditions for Detecting Blood Group Antibodies by the Antiglobulin Test, Vox Sang. 9: 385–395 (1964).

Elliot, M. et al. Influence of Ionic Strength on the Serologic Behavior of Red Cell Isoantibodies, Vox Sang. 9: 396–414 (1964).

Moore, H. C. et al. The Effects of Ionic Strength on Antibody Uptake with Special Reference to the Antiglobulin Test, Ortho Second Internat. Symp. on "The Nature and Significance of Complement Activation", Raritan. N.J., 1979.

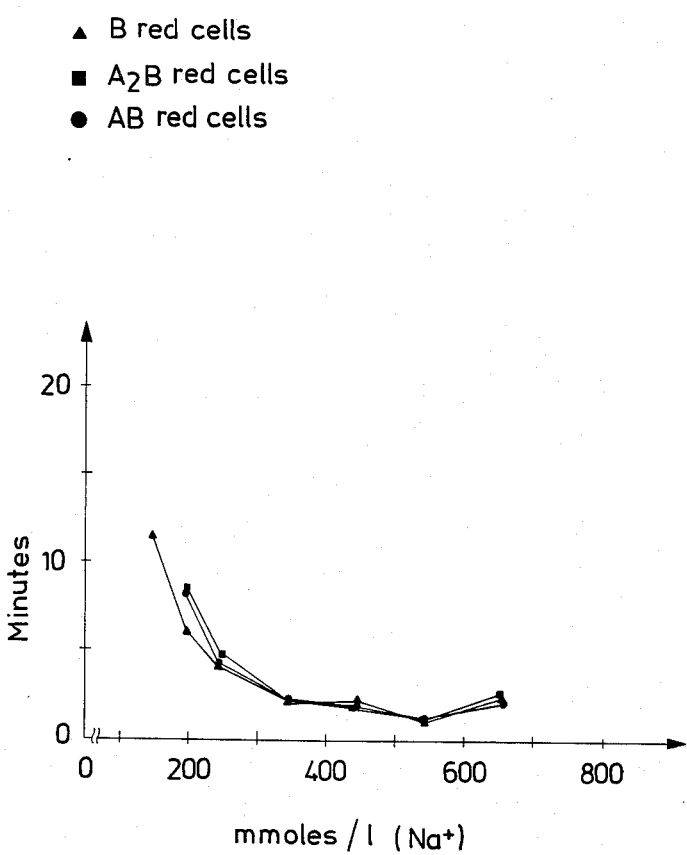

MONOCLONAL ANTIBODY FORMULATION FOR DIAGNOSTIC USE

The present invention relates to an aqueous formulation containing monoclonal antibodies active e.g. against human red cell antigens.

The expectation that monoclonal antibodies will be able to replace conventional polyclonal antibodies in routine ABO grouping has been questioned (Anstee, D. J.: "Characterization of human blood group alloantigens", Monoclonal antibodies in clinical medicine, [Ed. McMichael, A. J.; Fabre, J. W. Academic Press, London 1982],pp. 237-249). Recently several attempts to produce this type of antibody were reported, in which tissue culture cells from human colon carcinoma (Voak, D., "Monoclonal anti-A from a hybrid-myeloma: Evaluation as a blood grouping reagent", Vox Sang. 39: 134-140 [1980]), whole red cells (Edelman, L., et al, "Thermodynamic and immunological properties of a monoclonal antibody to human blood group A", Immunology 44: 549-554 [1981]), and Majdic, O., et al, "Hybridomas secreting monoclonal antibodies to human group A erythrocytes", Immunobiology 156: 226-227 [1979]), and native (Sacks, S. H., et al, "Monoclonal anti-B as a new blood-typing reagent", Vox Sang. 40: 99-104 [1981]) and synthetic (Bundle, D. R., et al, "Hybridomas specific for carbohydrates; Synthetic human blood group antigens for the production, selection, and characterization of monoclonal typing reagents", J. Immunol. 129: 678-682 [1982]) blood group active glycoproteins were used as immunogens using various immunization procedures. Some of the antibodies were claimed to have satisfactory quality for clinical use (Voak, D., et al, "Monoclonal anti-A and anti-B: Development as cost-effective reagents", Med. Lab Sci. 39: 109-122 [1982]), but in most cases, however, the titre was low and the reactions with weak subgroups were inadequate.

The present invention has for its purpose to provide an aqueous formulation containing monoclonal antibodies active against human red cell antigens, which formulation in clinical use shows improved performance when used as a blood grouping reagent as compared to conventional polyclonal antibodies.

In connection with research and experiments it has now been surprisingly found, that the presence in the aqueous antibody formulation of a soluble salt in a concentration of not less than about 200 mmoles per liter, will bring about a better titre and more distinct reactions when using the formulation. The monoclonal reagents according to the invention thus perform extremely well, both in manual and in automated blood grouping.

It is preferred to use a concentrated soluble salt in the formulation within the range from about 250 mmoles per liter to about 650 mmoles per liter, and the range of from about 350 to about 550 mmoles per liter is particularly preferred. The latter range corresponds to an osmolality of 700 to 1100 mosm.

As soluble salts it is preferred to use salts of the alkali or alkaline earth metals. The alkali metals are particularly preferred, especially those having a halide, such as chloride, as a counter ion. Sodium and potassium chlorides are most suitable to use as soluble salts, sodium chloride being particularly preferred. Among other salts there may be mentioned potassium chloride, calcium chloride, potassium iodide, magnesium chloride, magnesium sulphate, etc.

The invention is particularly applicable to blood grouping wherein the monoclonal antibodies are directed against the antigens of blood groups AB, or A,B. The formulation is preferably presented in the form of an aqueous solution.

The formulation of this invention may contain, in addition to monoclonal antibodies and the soluble salt also other ingredients conventional in the art mainly originating from the culture medium. The invention is, however, independent of variations in details concerning such conventional ingredients and is applicable to all aqueous formulations containing monoclonal antibodies of clinical use.

The invention will now be further described by way of illustration in the following experimental section drawn to specific embodiments. It must be noted, however, that the invention is not limited to any specific features disclosed in the experimental section but is limited only by the scope defined in the appended patent claims.

In the experiments, whole red cells, red cell membranes or soluble blood group substances prepared from individuals with blood group $A_1$, $A_2$, B or $A_2B$, were used as immunogens, and a high dose booster protocol (Stähli, C., et al, "High frequencies of antigen-specific hybridomas; Dependence on immunization parameters and prediction by spleen cell analysis", J. Immunol. Meth. 32: 297-304 [1980]) was adopted in most of the experiments. A large number of mouse-mouse hybridomas secreted antibodies with anti-A, anti-B and anti-AB specificity and several of these antibodies were shown to be superior to human polyclonal testsera, both in manual and in automated blood grouping.

EXPERIMENTAL SECTION

Mice

Female mice of the inbred Balb/cABom strain were obtained from G1 Bomholtgaard, Ry, Denmark. The mice were five to nine weeks old when first primed with antigen. They were kept on a standard pellet diet and water ad lib.

Antigens

Purified human ovarian cyst fluids glycoproteins from blood group $A_1$, $A_2$ and B individuals were gifts from Drs. W. M. Watkins and E. A. Kabat. Red cells from normal blood donors of blood group $A_1$, $A_2$ and $A_2B$ were used, either as 10% (v/v) suspensions in saline or as membranes (Dodge, J. T., et al, "The preparation and chemical characteristics of hemoglobin-free ghosts of human erythrocytes", Arch. Biochem. Biophys. 100: 119-130 [1963]) and suspended (10%, w/v) in saline.

Immunization procedure

Immunizations were performed according to the protocol in Table I. A final high-dose booster schedule (Stähli, C., et al, "High frequencies of antigen-specific hybridomas; Dependence on immunization parameters and prediction by spleen cell analysis", J. Immunol. Meth. 32: 297-304 [1980]) was usually followed when soluble blood group substances were used as antigens. With red cells, a shorter schedule with two consecutive intraperitoneal injections without adjuvant was mostly adopted. A few experiments were peformed using a single injection of antigen with fusion during the primary response.

Hybridoma techniques

Cell fusion, cloning and cultivation of hybridoma cell lines were performed according to standard procedures (Nowinski, R. C., et al, "The isolation of hybrid cell lines producing monoclonal antibodies against the p15[E] protein of ecotropic murine leukemia", Virology 93: 111-126 [1979]); Kennett, R. H., Monoclonal antibodies [Ed Kennett, R. H.; McKearn, T. J., Bechtol, K. B.] Plenum Press, New York 1980, pp. 365-367; and Fazekas de St. Groth, S., et al, "Production of monoclonal antibodies: Strategy and tactics", J. Immunol. Meth. 35: 1-21 [1980]). Myeloma cell lines SP2/0, P3-NS1 Ag-4, or P3x63 Ag-8-653.1 were used. Ascitic fluid was produced in Pristane ® (Aldrich, Beerse, Belgium)-treated mice.

Selection of antibodies and preparation of reagents

The culture medium from growing hybridomas was tested for haemagglutinating antibodies in microtitre plates (Linbro, Hamden Conn., USA) with red cells of different ABO groups, and in ELISA (Engwall, E., et al, "Enzyme-linked immunosorbent assay, ELISA III. Quantitation of specific antibodies by enzyme-labeled anti-immunoglobulin antigen-coated tubes", J. Immunol. 109: 129-135 [1972]), using microtitre plates (Microelisa ® immulon, Dynatech GmbH, Plachingen, W Germany) coated with blood group active glycoproteins. Ascitic fluids and tissue culture medium from expanded cultures were centrifuged to remove cellular debris. Tissue culture supernatants were decolourized by passage through a charcoal column. Sodium chloride (see also results), and sodium azide (0.1%) were added. Sodium was determined by flame photometry and osmolality by freezing point depression. The solutions were sterilized by filtration and stored at 4° C.

Isotype determination

The antibody isotype was determined by double diffusion (Ouchterlony, O., "Diffusion-in-gel methods for immunological analysis I", Progr. Allergy 5: 1-78 [1985]) using rabbit anti-mouse IgG1, IgG2a, IgG2b and IgM antisera, obtained from Miles, Elkhart, Ind. USA.

Agglutination tests

Manual tests were performed using undiluted culture medium or ascitic fluid diluted in 0.9% NaCl and 5% red cell suspensions which were incubated at room temperature, either on tiles for 20 min or in tubes for 1 h. Reactions were read against a well-lit backgroud, and positive reactions were graded from (+) to 4+. Red cell samples from healthy blood donors, newborn infants (cord samples) and patients were tested. In titration studies, twofold serial dilutions with saline were performed. Tube techniques with 1 h incubation were used. Avidity testing was performed both on slides with 40–50% red cell suspensions in homologous serum and on tiles with 5% red cell suspensions in saline. Agglutination strength was recorded at 30, 60, 90 and 120 sec. Specificity testing was performed using a large panel (35 donors) of extensively phenotyped cells. Standard two-step papain and bromelin methods, and saline testing were used in tube techniques with incubation at 4°, 22° and 37° C. The reactions were read microscopically. For comparison, 20 commercial polyclonal testsera of human origin (subsequently called polyclonal sera) were also analysed. Automated testing was performed with the Groupamatic 360 system using antibody diluted in saline and bromelinized cells in a standard procedure (Messeter, L., et al, "Automated blood grouping of patients and blood donors using Groupamatic 360 S and a separate minicomputer", Vox Sang. 33: 116-123 [1977]) Helix pomatia extract (Biotest, Frankfurt, Germany) was used for automated A-grouping. In addition to the automated evaluation, a visual check was also performed on all reactions.

RESULTS

The data from 18 fusions are complied in Table II. Ten fusions were performed after immunization with blood group active substances and eight using red cells or red cell membranes as antigen. Most fusions gave rise to several hybridomas that produced ABO-specific antibodies, but the majority of these antibodies were not agglutinating or only very weakly so. The specificity was in these cases determined with ELISA and these results will be published elsewhere. Immunization with A or B substances gave rise only to anti-A or anti-B antibodies, respectively, whereas red cell immunization also resulted in anti-AB and anti-N antibodies and several antibodies of hitherto unknown specificity.

During the experiments it was surprisingly found that an increase in salt concentration increased the antibody avidity as measured by the time to obtain a 4+ reaction. Although the observation was made in connection with using sodium chloride as a soluble salt similar effects were observed with other salts, such as KCl, $CaCl_2$, KI, $MgCl_2$, $MgSO_4$. However, since none of the other salts was better than sodium chloride this salt was selected as an additive.

In the appended FIGURE there is shown a diagram wherein the time for obtaining complete haemagglutination is plotted against the concentration of sodium chloride. The diagram in the FIGURE shows the reactions of anti-B 6.1.1. at various salt concentrations, and the supernatant was initially dialyzed against 0.1M sodium phosphate buffer pH 7.5. Without addition of salt, the pH optimum was found in the range of 6.5 to 7.5, but when the salt was added this pH optimum was broadened, and complete reactions were obtained most rapidly if the sodium ion concentration was between 350 and 550 mmoles/l, giving an osmolality of 700 to 1100 mosm.

A total of seven hybridomas were selected for further study: three that produced anti-A, two anti-B and two anti-AB. All seven were IgM antibodies and their specificity was confirmed with ELISA. One of the hybridoma cell lines (5.1.2, producing anti-AB) was lost due to infection and is therefore not included in all tests. Both the tissue culture supernatant and ascitic fluid produced by these hybridomas were used in this study, but most of the agglutination experiments have been performed with supernatants. The results of the manual agglutination tests are given in Tables III–V.

Blood samples from individuals with blood groups $A_1$, $A_2$, $A_1B$, B and O were studied (Table III). All monoclonal reagents gave potent reactions quite comparable to those of the polyclonal sera except 1.1.1, which had agglutinating properties similar to a *Dolichos biflorus* extract.

Table IV shows the results of agglutination tests with blood samples from 10 $A_2B$ donors. With red cells of this type, both of the monoclonal anti-A sera and the anti-A,B were clearly superior to the polyclonal sera tested. The reactions with monoclonal and polyclonal anti-B were of equal strength (4+) and are not given in the Table. Table V shows reactions with weak ABO variants. Both monoclonal anti-A reagents gave positive reactions with the two $A_x$ samples after 20 min incubation at 22° C. After incubation for 1 h in tubes, the polyclonal sera also gave (+) to 1+ reactions with the $A_x$ cells, but under these conditions the monoclonal sera gave 1+ to 2+ reactions. Both monoclonal anti-A reagents gave weak reactions with one of the $A_{el}$ samples but did not react with the other. None of the polyclonal reagents reacted with these cells. The only anti-B reagent to react with a $B_3$ sample (classified according to Race and Sanger (Race, R. R., et al, Blood Groups in Man. 5th Ed. [Blackwell, Oxford 1968] p. 23) was the monoclonal reagent 6.1.1. after incubation for 1 h at 4° C. and centrifugation (500 g, 60 sec). The monoclonal anti-A,B reacted more strongly than the polyclonal sera with the $A_3B$ sample and the A subgroups other than $A_x$.

The results of automated ABO blood grouping are given in Table VI. Each batch of samples was first analyzed using the routine reagents and was then retested using the monoclonal antisera. The number of refusals due to weak reactions were of the same order of all reagents.

All the reagents tested were completely specific, except the anti-AB 5.1.2 which gave weak ((+) to 1+) reactions with enzyme-treated group 0 cells. All other monoclonal reagents were negative with these cells.

In avidity testing with 40-50% red cell suspensions, the antibody 2.3.2 was more avid than polyclonal anti-A, particularly with $A_2B$ red cells, and the anti-B antibody 6.1.1 was more avid than polyclonal anti-B, particularly with $A_1B$ red cells. The monoclonal antibodies 1.4.1 and 3.1.1 reacted more slowly than the polyclonal sera, but the time to obtain a 4+ reaction was within the two minute limit set in the European Agreement (European Agreement on the exchanges of blood-grouping reagents, European Treaty Series No. 39 [Council of Europe, Strasbourg, 1962]). When tested with 5% red cell suspensions on tiles, the avidity generally was higher with monoclonal than with polyclonal sera.

A monoclonal and a polyclonal antibody of each specificity (A; B; AB) were tested for ability to agglutinate BAlb/c mouse erythrocytes. As can be seen in Table VII, none of the monoclonal reagents reacted with the murine cells, whereas the polyclonal anti-B and anti-AB gave weakly positive reactions.

A series of fusions was performed using several immunization and fusion protocols and a number of potentially suitable antigens. Although a total of 18 fusions was carried out, the use of three different immunization routes, three different myeloma cell lines and three different types of antigen (Table I) precludes the definition of an optimum fusion schedule. However, certain observations can be made. In four fusions using immunization schedule 3 relatively few positive hybridomas were obtained, all lacking heamagglutinating activity (in the ABO system). It should be pointed out, however, that in three of four fusions using this schedule, NS1 myeloma cells were used, which yielded fewer hybridomas than either 653 or SP2/0 cells.

Both immunization Schedule 1 using blood group substances, and Schedule 2 using erythrocytes gave a large number of positive hybridomas, both 653 and SP2/0 cells being equally efficient. However, the number of haemagglutination positive hybridomas varied considerably with both cell types. Of the eight "useful" clones obtained, five came from fusions with 653 cells, two with SP2/0 cells and one from NS1 cells, the latter being one of only two haemagglutination positive hybridomas obtained from five fusions with these cells.

Both tissue culture supernatants and ascitic fluids from each hybridoma were studied. The advantage of ascitic fluid antibodies is their high concentration in this fluid which enables them to be used in high dilution. This dilution also has the effect of diluting the mouse's own natural antibodies which have been shows to react with determinants expressed on human fetal and other glycoproteins (Gooi, H. C., et al, "Natural antibodies as contaminants of hybridoma products", Biochem. Biophys. Res. Comm. 106: 539–545 [1982]). The concentration of the antibodies from ascitic fluid in this study was too low to allow the required high dilution, possibly due to the in vivo breakdown of the IgM molecules formed by the hybridoma cells (Lennox, S., Personal communication) supernatants were sufficiently potent to be used in routine blood grouping, so were generally preferred in haemagglutination tests.

The specificities of the haemagglutinating antibodies obtained from each fusion using mice immunized with blood group substances was, as expected, specific for the particular blood group, with the exception of one antibody of unknown specificity from fusion 1.4 and an anti-A($A_1$) obtained from fusion 2.3 using blood group $A_2$ substance. The latter may be explained by the presence of an $A_1$ domain in the $A_2$ substance, i.e. a small region in the glycoprotein having a higher than normal density of A determinants.

Immunization with red cells gave a more complex picture of haemagglutinating antibody synthesis. No fusion using $A_2$, $A_2B$ or $A_1+A_2$ red cells resulted in the formation of an anti-A. Most notable was the formation of 21 anti-A($A_1$), two anti-AB and two antibodies of unknown specificity from a fusion (5.1) using $A_2$ cells. Also notable was the formation of 10 anti-B, one anti-AB and 12 unknown but no anti-A from fusion 6.1 using $A_2B$ cells.

The production of an anti-B antibody in mice is of interest since most mouse strains, including Balb/c are considered to have a blood group B-like antigen on their erythrocytes, and thus are expected not to produce an anti-B (Sacks, S. H., et al, "Monoclonal anti-B as a new blood-typing reagent", Vox Sang. 40: 99–104 [1981]). Mouse red cells were tested with the monoclonal and polyclonal reagents (Table VII) and were found to react weakly with the polyclonal anti-B and anti-A,B, but not with the anti-A. None of the corresponding monoclonal reagents reacted with the murine cells, which explains why these antibodies can be produced in mice. The mouse "B-like" antigen is therefore recognized by other antibodies in the polyclonal anti-B sera which are by definition absent from the monoclonal reagents.

The addition of salts to the monoclonal antibodies increases the rate of the agglutination reaction, which remains constant over a relatively wide range, but causes dramatically reduced avidity outside certain limits. Isotonic saline (0.15M) is generally used for blood grouping purposes, but it is well known that the rate of the reaction between polyclonal IgG antibodies and antigen is increased by a reduction of ionic strength from 0.15M to 0.03M (Hughes-Jones, N. C., et al, "Optimal conditions for detecting blood group antibodies by the antiglobulin test", Vox Sang. 9: 385–395 [1964] and Elliot, M., et al, "Influence of ionic strength on the serologic behaviour of red cell isoantibodies", Vox Sang. 9: 396–414 [1964]). The reaction between purified polyclonal IgM anti-A and A red cells, on the other hand, is not increased in media of low ionic strength (Moore, H. C., et al, "The effects of ionic strength on antibody uptake with special reference to the antiglobulin test", Ortho second internat. symp. on "The nature and significance of complement activation", Raritan, N.J. 1976). The mechanism of changed association rates in media with different ionic strengths is not known and either antigen or antibody could be affected. Although the invention is not to be bound by any theory a conceivable explanation could be that the addition of salts might cause conformational changes favouring binding to the antigen combining site.

Manual tests (Tables III–V) using 5% red cell suspensions indicated that the monoclonal antibodies chosen for study were all as potent and specific as the polyclonal reagents when tested with $A_1$, $A_2$, $A_1B$, B and O cells, and A and B cord cells (Table III). The exception was clone 1.1.1 which has the characteristics of an anti-A antibody. Using $A_2B$ cells the monoclonal anti-A and anti-AB reagents were clearly better than the corresponding polyclonal sera (Table VI), whereas all the anti-B reagents gave a complete reaction. More demanding tests using erythrocytes with weaker A or B antigens (Table V) indicated that when there were any reactions at all, the monoclonal anti-A and anti-B reagents were slightly better. The reactions of the anti-AB sera were rather variable.

In automated grouping the performance of the monoclonal reagents was also excellent (Table VI). The monoclonal anti-A performed as well as the Helix extract which is normally used in automated grouping since the reactions of polyclonal anti-A reagents are too weak with $A_2B$ cells (Messeter, L., et al, "Automated blood grouping of patients and blood donors using Groupamatic 360 S and a separate minicomputer", Vox Sang. 33: 116–123 [1977]). The weak, apparently non-specific reaction seen with enzyme-treated group O red cells and the monoclonal anti-AB reagent in specificity testing was not observed in automated grouping of more than 11000 samples in the Groupamatic system in which bromelinized red cells are used.

Using a 40–50% red cell suspension, some of the monoclonal reagents were less avid than the polyclonal reagents, but this could easily be remedied by concentrating the monoclonal antibody supernatants five-tenfold. However, this is unnecessary (Voak, D., et al, "Monoclonal anti-A and anti-B: Development as cost-effective reagents", Med. Lab. Sci. 39: 109–122 [1982]) for routine use.

So far, the monoclonal reagents have shown no loss of titre when stored at 4° C. for at least one year or at room temperature for over two months.

It is to be understood that the invention is not to be limited to the exact details of operation or exact antibodies, antigens or procedures shown and described, as obvious modifications and equivalents will be apparent to one skilled in the art, and the invention is therefore to be limited only by the full scope of the appended claims, including the application of the doctrine of equivalents thereto.

TABLE I

Immunization and fusion schedule

| Day | Final high-dose booster (substances) 1. | Immunization with cells 2. | Primary response (cells or substances) 3. |
|---|---|---|---|
| 1 | 50 μg + CFA SC | 0.5 ml IP | 0.5 ml/50 μg IP FUSION |
| 5 | | | |
| 15 | 50 μg + IFA IP | 0.5 ml IP | |
| 19 | | FUSION | |
| 29 | 50 μg IP | | |
| 30 | 400 μg IP | | |
| 31 | 400 μg IP | | |
| 32 | 400 μg IP | | |
| 33 | FUSION | | |

Abbreviations:
CFA Complete Freund's adjuvant (Difco, Detroit, Mich. USA)
IFA Incomplete Freund's adjuvant (Difco)
SC Subcutaneous injection
IP Intraperitoneal injection

TABLE II

Compiled fusion results

| Fusion Number | Antigen | Immunization schedule* | Myeloma cell line | Total Number of hybridomas | Hybridomas positive in haemagglutination | Haemagglutinating specificity | Designation of useful haemagglutinating clones |
|---|---|---|---|---|---|---|---|
| 1.1 | $A_1$ substance | 1 | NS1 | 92 | 2 | Anti-A($A_1$) | 1.1.1 |
| 1.2 | $A_1$ substance | 3 | NS1 | 118 | 0 | | |
| 1.3 | $A_1$ substance | 1 | 653 | 380 | 8 | Anti-A($A_1$) | |
| 1.4 | $A_1$ substance | 1 | 653 | 82 | 3 | Anti-A | 1.4.1 |
| | | | | | 1 | Unknown | |
| 1.5 | $A_1$ substance | 1 | SP2/0 | 73 | 1 | Anti-A($A_1$) | |
| 1.6 | $A_1$ substance | 1 | 653 | —** | | | |
| 2.1 | $A_2$ substance | 1 | NS1 | 37 | 0 | | |
| 2.2 | $A_2$ substance | 1 | SP2/0 | 100 | 0 | | |
| 2.3 | $A_2$ substance | 1 | SP2/0 | 432 | 29 | Anti-A | 2.3.2 |
| | | | | | 25 | Anti-A($A_1$) | |
| 3.1 | B substance | 1 | 653 | 84 | 6 | Anti-B | 3.1.1 |
| 4.1 | $A_1$ membranes | 3 | NS1 | 0 | | | |
| 4.2 | $A_1$ membranes | 3 | NS1 | 14 | 0 | | |
| 5.1 | $A_2$ red cells | 2 | 653 | 160 | 21 | Anti-A($A_1$) | |
| | | | | | 2 | Anti AB | 5.1.2 |
| | | | | | 2 | Unknown | |
| 5.2 | $A_2$ red cells | 2 | 653 | 192 | 1 | Unknown | |
| 5.3 | $A_2$ red cells | 2 | SP2/0 | 384 | 1 | Anti-N | 5.3.1 |
| 6.1 | $A_2B$ red cells | 2 | 653 | 387 | 10 | Anti-B | 6.1.1 |
| | | | | | 1 | Anti AB | 6.1.5 |
| | | | | | 12 | Unknown | |
| 6.2 | $A_2B$ red cells | 2 | 653 | 175 | —** | | |

TABLE II-continued

Compiled fusion results

| Fusion Number | Antigen | Immunization schedule* | Myeloma cell line | Total Number of hybridomas | Hybridomas positive in haemagglutination | Haemagglutinating specificity | Designation of useful haemagglutinating clones |
|---|---|---|---|---|---|---|---|
| 7.1 | $A_1 + A_2$ red cells | 3 | SP2/0 | 10 | 0 | | |

*See Table I
**Lost in tissue culture

TABLE III

Agglutination reactions with red cells of different ABO groups

| | $A_1$ | $A_2$ | $A_{cord}$ | $A_1B$ | B | $B_{cord}$ | O |
|---|---|---|---|---|---|---|---|
| Anti-A | | | | | | | |
| 1.1.1* | 4 | (+) to 1 | (+) to 4 | 4 | neg | neg | neg |
| 1.4.1* | 4 | 4 | 3 to 4 | 4 | neg | neg | neg |
| 2.3.2** | 4 | 4 | 4 | 4 | neg | neg | neg |
| Polyclonal I | 4 | 4 | 4 | 4 | neg | neg | neg |
| Polyclonal II | 4 | 4 | 3 to 4 | 4 | neg | neg | neg |
| Anti-B | | | | | | | |
| 3.1.1* | neg | neg | neg | 4 | 4 | 4 | neg |
| 6.1.1* | neg | neg | neg | 4 | 4 | 4 | neg |
| Polyclonal I | neg | neg | neg | 4 | 4 | 4 | neg |
| Polyclonal II | neg | neg | neg | 4 | 4 | 4 | neg |
| Anti AB | | | | | | | |
| 5.1.2*** | 4 | 4 | 4 | 4 | 4 | 4 | neg |
| 6.1.5** | 4 | 4 | 4 | 4 | 4 | 4 | neg |
| Polyclonal I | 4 | 4 | 4 | 4 | 4 | 4 | neg |
| Polyclonal II | 4 | 4 | 4 | 4 | 4 | 4 | neg |

*Ascites, diluted 1:250
**Supernatant
***Ascites, diluted 1:200

TABLE IV

Agglutination reactions with erythrocytes from 10 $A_2B$ persons

| | 1 | 2 | 3 | 4 | 5 | 6 | 7 | 8 | 9 | 10 | Score |
|---|---|---|---|---|---|---|---|---|---|---|---|
| Anti-A | | | | | | | | | | | |
| 1.4.1 | 4 | 4 | 4 | 4 | 3 | 3 | 4 | 3 | 4 | 4 | 37 |
| 2.3.2 | 4 | 4 | 4 | 4 | 3 | 4 | 4 | 3 | 3 | 3 | 36 |
| Polyclonal I | 3 | 2 | 2 | 3 | 1 | 3 | 2 | 3 | 2 | 2 | 23 |
| Polyclonal II | 3 | 3 | 3 | 3 | 2 | 3 | 3 | 3 | 3 | 3 | 29 |
| Polyclonal III | 3 | 3 | 3 | 3 | 2 | 3 | 3 | 3 | 2 | 2 | 27 |
| Polyclonal IV | 3 | 3 | 3 | 3 | 2 | 3 | 2 | 3 | 3 | 3 | 28 |
| Polyclonal V | 3 | 3 | 3 | 3 | 3 | 3 | 3 | 3 | 3 | 3 | 30 |
| Polyclonal VI | 4 | 3 | 3 | 3 | 3 | 3 | 3 | 3 | 3 | 3 | 31 |
| Anti AB | | | | | | | | | | | |
| 6.1.5 | 4 | 4 | 4 | 4 | 3 | 4 | 4 | 3 | 3 | 3 | 36 |
| Polyclonal I | 4 | 4 | 4 | 4 | 3 | 4 | 4 | 3 | 3 | 3 | 36 |
| Polyclonal II | 2 | 2 | 3 | 3 | 3 | 4 | 3 | 3 | 3 | 3 | 29 |
| Polyclonal III | 3 | 3 | 3 | 3 | 3 | 4 | 3 | 3 | 3 | 3 | 31 |
| Polyclonal IV | 2 | 3 | 3 | 3 | 3 | 3 | 3 | 3 | 3 | 2 | 28 |
| Polyclonal V | 3 | 3 | 3 | 3 | 3 | 3 | 3 | 3 | 3 | 3 | 30 |
| Polyclonal VI | 3 | 3 | 3 | 3 | 3 | 3 | 3 | 3 | 3 | 3 | 30 |

TABLE V

Agglutination reactions with weak ABO variants

| | $A_3B$ | $A_x$ | $A_x$ | $A_m$ | $A_{end}$ | $A_{el}$ | $A_{el}$ | $B_3$ | $B_3$ |
|---|---|---|---|---|---|---|---|---|---|
| Anti-A | | | | | | | | | |
| 1.2.1 | 1* | (+)* | (+)* | neg | neg | neg | (+)* | neg | neg |
| 2.3.2 | 2* | 1* | 1* | neg | neg | neg | (+)* | neg | neg |
| Polyclonal I | 1* | w | neg | neg | neg | neg | neg | neg | neg |
| Polyclonal II | (+)* | neg | neg | neg | neg | neg | neg | neg | neg |
| Anti-B | | | | | | | | | |
| 3.1.1 | 4 | neg | neg | neg | neg | neg | neg | neg | neg |
| 6.1.1 | 4 | neg | neg | neg | neg | neg | neg | (+)* | neg |
| Polyclonal I | 4 | neg | neg | neg | neg | neg | neg | neg | neg |
| Polyclonal II | 4 | neg | neg | neg | neg | neg | neg | neg | neg |
| Anti AB | | | | | | | | | |
| 6.1.5 | 4 | (+)* | neg | (+)* | 1* | 1* | neg | neg | 1* |
| Polyclonal I | 3 | 2* | 2* | neg | neg | neg | neg | (+)* | (+)* |
| Polyclonal II | 3 | 1* | 1* | neg | neg | neg | neg | neg | neg |

*Mixed field appearance
w = weak reaction

TABLE VI

A comparison of automated ABO grouping using commercial reagents and the monoclonal antisera. The reagents were diluted as indicated.

| Blood Group | Accepted results | Weak reactions Routine reagents | | | Monoclonal reagents | | | Non-specific reactions |
|---|---|---|---|---|---|---|---|---|
| | | Anti-A Helix 1:2000 | Anti-B polycl. 1:50 | Anti AB polycl. 1:50 | Anti-A 1.4.1 1:10 | Anti-B 3.1.1 1:10 | Anti AB 6.1.5 1:5 | |
| A | 5235 | 7 | | 4 | 10 | | 5 | 0 |
| B | 1211 | | 3 | 2 | | 4 | 4 | 0 |
| AB | 572 | 16 | | 3 | 4 | 3 | 2 | 0 |
| O | 4461 | | | | | | | 0 |
| | 11479 | | 35 | | | 32 | | 0 |

TABLE VII

| Agglutination reactions with Balb/c mouse red cells | | | | | |
|---|---|---|---|---|---|
| | Mouse number | | | | |
| Reagent | 1 | 2 | 3 | 4 | 5 |
| Anti-A | | | | | |
| 1.2.1 | — | — | — | — | — |
| Polyclonal I | — | — | — | — | — |
| Anti-B | | | | | |
| 3.1.1 | — | — | — | — | — |
| Polyclonal I | 1* | 1* | 1* | 1* | 1* |
| Anti AB | | | | | |
| 6.1.5 | — | — | — | — | — |
| Polyclonal I | 2* | 2* | 2* | 2* | 2* |

*Mixed field appearance

I claim:

1. A method for identifying ABO blood groups comprising contacting a member selected from the group consisting of whole red cells, red cell membranes and soluble group substances with an aqueous formulation comprising monoclonal antibodies active against cell-bound antigens of blood group A, B or AB and a soluble salt selected from the group consisting of salts of the alkali and alkaline earth metals in a concentration within the range of from 250 mmoles/liter to about 650 mmoles/liter.

2. A method according to claim 1, wherein said concentration is within the range of from about 350 m moles/liter to 550 mmoles/liter.

3. A method according to claim 1, wherein said salt is selected from the alkali metals.

4. A method according to claim 3, wherein said salt has a halide counter ion.

5. A method according to claim 1, wherein said salt is selected from the group consisting of NaCl, KCl, $CaCl_2$, KI, $MgCl_2$ and $MgSO_4$.

6. A method according to claim 5, wherein said salt is NaCl.

7. A method according to claim 1, wherein the aqueous formulation is in the form of a solution.

8. A method according to claim 7, wherein the aqueous formulation is in the form of a solution and wherein the soluble salt is sodium chloride.

9. An aqueous formulation comprising monoclonal antibodies active against cell-bound antigens of blood group A, B or AB and a soluble salt selected from the group consisting of NaCl, KCl, $CaCl_2$, KI, $MgCl_2$ and $MgSO_4$ in a concentration within the range of from 250 mmoles/liter to about 650 mmoles/liter.

* * * * *